United States Patent [19]

Müller

[11] 4,158,609

[45] Jun. 19, 1979

[54] PROCESS FOR THE CONTINUOUS CONVERSION OF PRODUCTS BY ENZYME ACTION

[76] Inventor: Hans Müller, Im Allmendli, 8703 Erlenbach, Switzerland

[21] Appl. No.: 865,621

[22] Filed: Dec. 29, 1977

Related U.S. Application Data

[63] Continuation of Ser. No. 723,882, Sep. 19, 1976, abandoned.

[30] Foreign Application Priority Data

Sep. 23, 1975 [CH] Switzerland ............... 12350/75

[51] Int. Cl.² ........................................... C12B 1/00
[52] U.S. Cl. ........................ 195/115; 195/31 F; 195/139
[58] Field of Search ............... 195/139, 115, 140, 127, 195/141, 143, 144, 108, 113, 119, 31 R, 21 F; 23/288 E; 210/321, 433

[56] References Cited

U.S. PATENT DOCUMENTS

| | | | |
|---|---|---|---|
| 3,642,580 | 2/1972 | Ghose | 195/33 |
| 3,694,314 | 9/1972 | Lloyd | 195/31 F |
| 3,720,583 | 3/1973 | Fisher | 195/115 X |
| 3,753,725 | 8/1973 | Williams et al. | 195/31 R |

OTHER PUBLICATIONS

O'Neill, et al., "An Ultrafiltration-Reactor System Using a Soluble Immobilized Enzyme," *Biotechnology and Bioengineering*, vol. 13, (1971), pp. 319-322.

Chain, et al., "Ultrafiltration of Biological Materials," *Process Biochemistry*, Sep., 1969), pp. 47-51.
Bowski et al., "Process Simulation of Sucrose Hydrolysis on Invertase in a Continuous Flow Stirred Tank/Ultrafiltration Reaction System," *Enzyme Engineering*, Wingard, ed., John Wiley & Sons, Interscience Publishers, NY, (1972) pp. 229-239.
Porter et al., "Membrane Ultrafiltration," *Chem. Tech.*, (Jan., 1971), pp. 56-63.
Michaels, "New Separation Technique for the CPI", *Chem. Eng. Progress*, vol. 84, No. 12, (1968), pp. 31-43.

Primary Examiner—Thomas G. Wiseman
Attorney, Agent, or Firm—Michael J. Striker

[57] ABSTRACT

Enzymated products are made in a continuous process by (a) continuously passing a substrate and an enzyme containing fermentation broth into a reaction zone, (b) continuously passing the converted product from in said reaction zone to a filtration zone for separation of the enzyme from said product, (c) continuously recycling enzyme remaining as the retentate in the filtration zone back into said reaction zone, and (d) continuously collecting the converted product received as the filtrate from said filtration zone, the said reaction zone and filtration zone forming a closed circulation circuit.

3 Claims, 2 Drawing Figures

PROCESS FOR THE CONTINUOUS CONVERSION OF PRODUCTS BY ENZYME ACTION

This is a continuation, of application Ser. No. 723,882, filed Sept. 19, 1976, now abandoned.

BACKGROUND OF THE INVENTION

The invention relates to a process for the continuous production of enzyme products particularly by means of extracellular enzymes.

Processes for effecting the conversion of products by means of enzymes disposed on carrier materials have been known. The difficulties encountered with the regeneration of water insoluble carrier supported enzymes have caused the attempts to obtain better results by using ultrafilters in the enzyme formation. When making proteolytic enzymes this resulted in higher enzyme activities in the fermentation broth (E. S. K. Chian et al., Process Biochem, 4 (9), 47 (1969)). The ultrafiltration with carrier disposed enzymes has been described in case of chymotrypsin by S. P. O'Neill et al., Biotechn. & Bioeng., 13, 319 (1971)).

None of these publications described a process for the continuous production of conversion products by means of enzymes.

The addition of pure enzyme to a substrate can be effected only in small amounts because of the high cost. Since the reaction speed is proportional to the enzyme concentration the reaction time is comparatively long. Besides the conversion product must be separated from the enzyme, byproducts and contaminations in a complicated process.

If immobilized (fixated) enzymes are used the filling and emptying of the columns is also difficult and the process cannot easily be automated. The control of the columns presents problems and the switching from one column to the other column is difficult.

SUMMARY OF THE INVENTION

It is therefore an object of the present invention to provide for a continuous process on an industrial scale for the production of enzyme products from a substrate.

The invention is based on the finding that a conversion process of this kind can be carried out in circulation by maintaining a high enzyme concentration in a reaction tank which is connected with an ultrafilter. The reaction product is then continuously removed from the reaction tank, the enzyme is retained and fresh product is continuously added. In this manner a high rate of conversion can be maintained with simultaneous retention of the enzyme.

Specifically this is accomplished by (a) continuously passing a substrate and an enzyme containing fermentation broth into a reaction zone, (b) continuously passing the converted product from in said reaction zone to a filtration zone for separation of the enzyme from said product, (c) continuously recycling enzyme remaining as the retentate in the filtration zone back into said reaction zone, and (d) continuously collecting the converted product received as the filtrate from said filtration zone, the said reaction zone and filtration zone forming a closed circulation circuit.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF SPECIAL EMBODIMENTS

Figure 1:
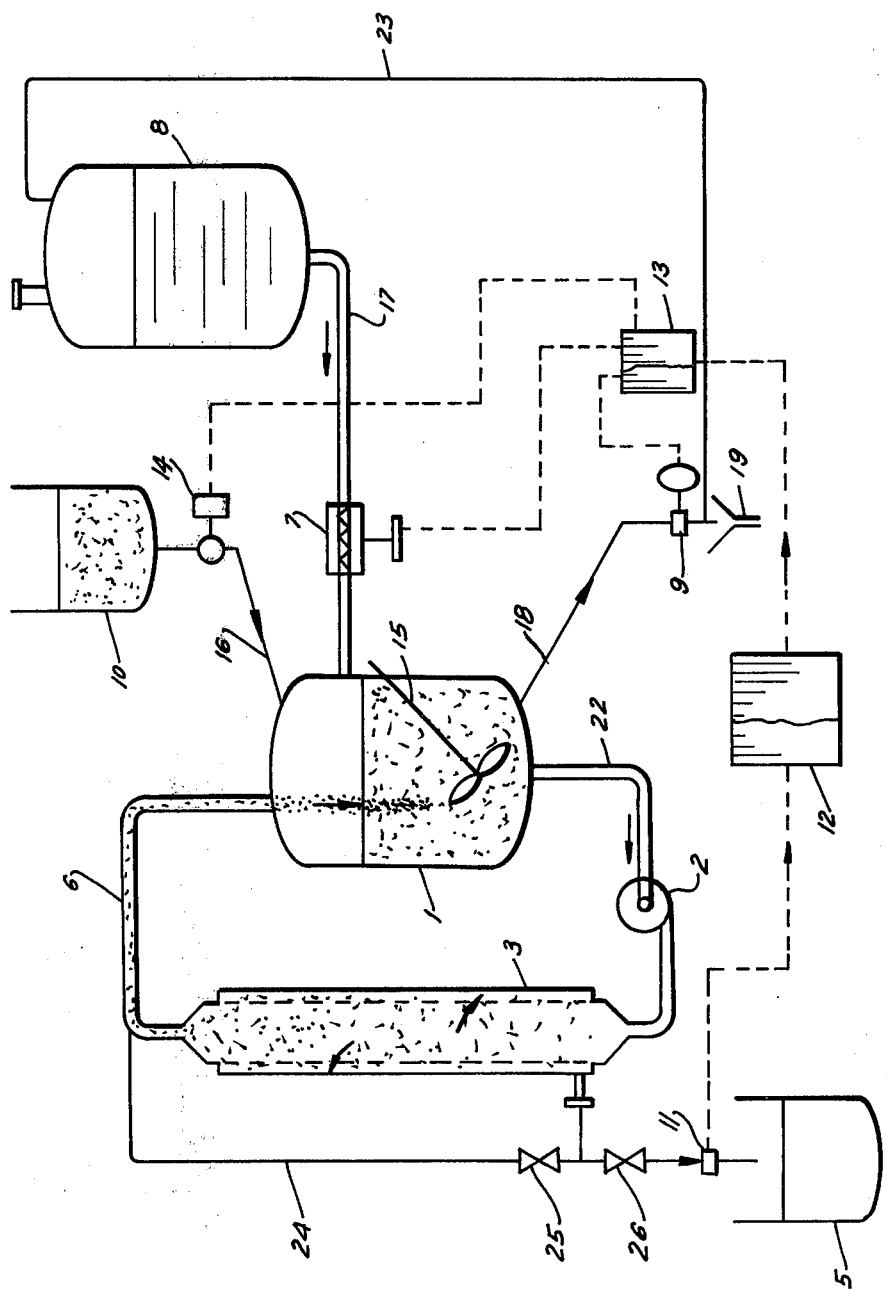
FIG. 1 is a schematic illustration of the process of the invention.

With reference particularly to FIG. 1, it will be seen that there is provided a reaction tank 1 in which is disposed a stirrer 15. Connected with the reaction tank is an ultrafilter 3. The discharge from the bottom portion of the reaction tank is effected through a duct 22 in which there is provided a pump 2. The duct leads into the bottom portion of the ultrafilter. Another duct 6 connects the top portion of the ultrafilter with the reaction vessel. The ultrafilter in turn has a discharge duct 4 for the filtrate. At the end of the discharge duct a device for removing specimens is provided which includes an analyzer 11.

A vessel 5 serves to receive the filtrate. The outlet for the harvest of a fermentor 10 is connected through a valve 14 and a conduit 16 with the reaction vessel 1.

The product to be converted is received from a supply tank 8 through a conduit 17 and a dosage pump 7 and is in this manner continuously passed into the reaction tank.

The entire process is automated by means of the analyzer 11, the regulator 12, the second analyzer with control valve 9, a second regulator 13 and a control valve 14, the regulators being automatic measuring and coated units.

The operation of the installation is as follows:

The product to be converted is received from the tank 8 and passed into the reaction vessel 1 together with the enzyme obtained from the fermentor 10. The pump 2 then circulates the solution or suspension formed in the tank through ultrafilter 3 which is provided with a semi-permeable membrane which is adapted to retain the enzyme and larger molecules. The filtrate leaves the ultrafilter via the duct 4 and contains the converted product which then is received in the collector 5. The enzyme solution is circulated back into the reaction vessel through the conduit 6.

The product to be converted is continuously supplied to the reaction vessel from the supply tank by means of dosage pump 7. The spent enzyme can either be drained from time to time completely or partly via the analyzer and valve 9 by means of the duct 18. Fresh enzyme is continuously added from the fermentor 10 via the conduit 16. These additions are in measured dosage according to the activity of the enzyme which is measured by means of a measuring and control device 13 which controls the enzyme addition by the valve 14. The addition of the fresh product from the tank 8 is controlled by the analyzer 11 and via the regulator 12 and the pump 7. New supply and discharge of enzyme from the reaction tank 1 or into the tank is controlled in accordance with the analysis obtained by the analyzer 9 and by means of the regulator 13 and the valve 14.

Insufficiently reacted product together with enzyme can be circulated back into the supply tank 8 through the duct 23. The fact that there may be a preliminary conversion because of the presence of enzyme in the tank 8 is without significance in this case.

The control of the formed filtrate is accomplished as indicated by the analyzer 11. If for instance in case of the desired degredation of the polysaccharide in an aqueous solution no degradation has been effected, for instance because of a poisoning of the enzyme, the analyzer will indicate only water and will be in the zero position. In that case the filtrate must be recycled in order to prevent a backing up in the discharge duct. This recycling can be accomplished through the duct 24 by closing the valve 26 and opening the valve 25. In this manner a filtrate is passed back into the reaction tank 1.

The analyzers referred to herein by reference numbers 11 and 9 may be conventional polarimeters.

While the analyzer 11 as just stated determines the completion of the conversion reaction in the permeate, the analyzer 9 continuously checks the activity of the enzyme in the reaction vessel 1. This control is effected by the analyzer 9 independently from the analyzer 11 although the latter by determining the amount of converted product in the filtrate of course provides results which have a bearing also on the activity of the enzyme. The analyzer 9 therefore constitutes an additional control.

The regulators 12 and 13 may be combined in one single device.

The analyzer 9 thus permits two modes of regulation. The enzyme may be entirely discharged into the drain 19. This will be done only if there is no further conversion product available or if the product and enzyme are so inexpensive to permit complete replacement. The other possible manner of regulation is that the product is recirculated through duct 23 into the initial supply tank 8.

The analyzer 9 thus has the principal object of controlling the enzyme supply by means of the valve 14 and through duct 16 from the enzyme supply tank 10 which regulation is carried out by means of the regulator 13 which like the regulator 12 may be a conventional electrically or electronically actuated control device.

The enzymes which may be used in the process of the invention may be immobilized enzymes, free enzymes of enzyme producing bacteria or enzymes produced thereby.

The enzyme reactions which can be carried out with the process and apparatus of the invention may for instance be the following:

(a) Degradation of higher molecular materials into lower molecular matters, for instance, degradation of polysaccharides into disaccharides and monosaccharides or degradation of disaccharides into monosaccharides, etc.

Figure 2:
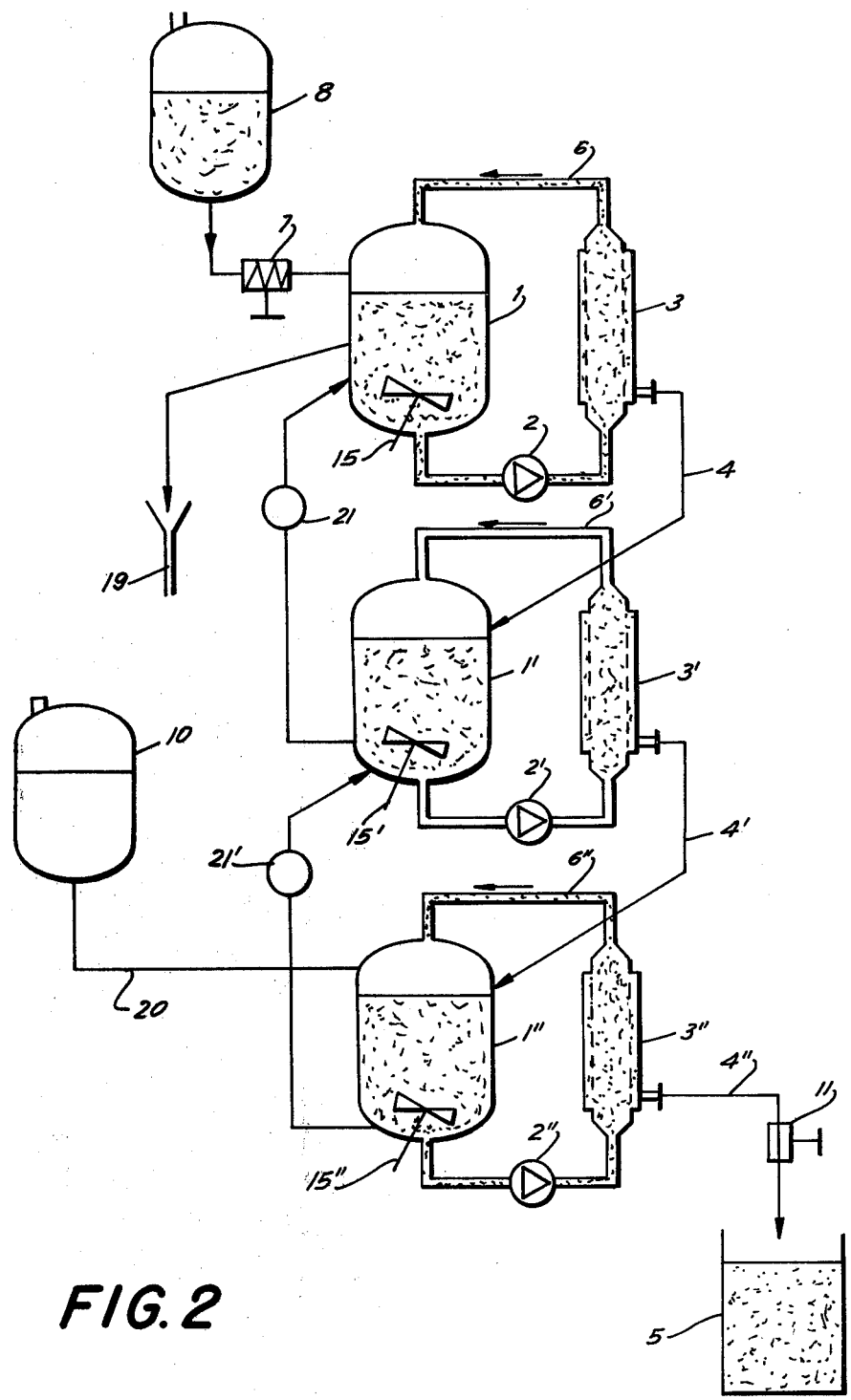
FIG. 2 illustrates a special embodiment useful particularly for the isomerization of chemical compounds of about equal molecules by means of enzymes and employing a counter-current arrangement.

(b) Isomerization of molecules in which case the degree of isomerization may be adjusted by the device of FIG. 1 or in which case a complete isomerization may be effected by the device shown in FIG. 2.

This latter installation comprises a multiplicity of reaction tanks 1, 1', 1" and corresponding ultrafilters 3, 3', and 3" which are arranged in series and through which the raw material and the enzyme are passed in countercurrent directions.

As the FIG. 2 shows the fresh product is supplied as in FIG. 1 from a supply tank 8 by means of a dosage device 7 and passed into the first reaction tank 1. The reaction product formed in the tank 1 is then circulated by means of the pump 2 through the ultrafilter 3 and back into the reaction tank via the duct 6. The device is different from the installation shown in FIG. 1 in that the filtrate from the ultrafilter 3 is passed through a duct 4 into the next reaction tank 1'. The same takes place with the filtrate obtained from the ultrafilter 3' which is passed through a duct 4' into the next reaction tank 1". The circulation conduits 6' and pump 2' and conduits 6" and pump 2" are arranged in the same manner as with the first reaction tank.

Each of the reaction tanks is also provided with a stirrer 15, 15' and 15".

The partly spent enzyme is also passed back from reaction tank 1' by means of the pump 21 into the reaction tank 1 and in a similar manner from the reaction tank 1" by means of pump 21' into reaction tank 1'.

There is also provided a discharge outlet 19 in a similar manner as in the installation shown in FIG. 1. There is also provided a supply tank for fresh fermentation broth to obtain fresh enzyme. This tank is indicated as in the installation of FIG. 1 by reference number 10 but in this case leads through duct 20 into the last of the series-connected reaction tanks that is into the tank 1". There is thus obtained a counter-current arrangement between the fresh enzyme and the fresh raw material.

The fresh enzyme can therefore react with maximum activity on the product in the last reaction tank 1" so as to cause a complete conversion.

The filtrate from the last ultrafilter 3" is passed through duct 4" to an analyzer 11 and from there may be passed to the storage tank 5 in a similar manner as in the installation shown in FIG. 1.

The installation of FIG. 2 is particularly intended for isomerization of chemical compounds by means of enzyme action. Thus the compounds used in this process should have equal molecular weight prior and after conversion or should result in a smaller molecular weight due to the conversion.

The installation shown in FIG. 2 will accomplish a still further improved use of the initial enzyme. For the purposes stated it is therefore a more specialized device.

Without further analysis the foregoing will so fully reveal the gist of the present invention that others can, by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process for the continuous conversion of products by enzyme action comprising the steps of:
  (a) continuously passing a substrate and an enzyme containing solution through a plurality of series-connected reaction zones in which the substrate is subjected to a conversion reaction by enzymes;
  (b) continuously passing the conversion product from each reaction zone through an ultrafiltration zone for separation of the enzyme as the retentate from said product before passing the product on to the next reaction zone;
  (c) continuously recycling enzyme remaining as the said retentate in each filtration zone back into the reaction zone from which product is fed into said ultrafiltration zone, and
  (d) continuously collecting the converted product received as the filtrate from the last of said plurality of series-connected filtration zones while passing back partly spent enzyme from each reaction zone to the next preceding reaction zone, the said reaction zones and filtration zones forming a closed circulation circuit and fresh substrate being continuously passed into the first of said reaction zones, fresh enzyme being continuously passed into the last of said reaction zones and causing a countercurrent flow in each reaction zone between the substrate and the enzyme supply.

2. The process of claim 1 wherein the substrate and solution in said reaction zones are subject to continuous agitation.

3. An apparatus for the continuous production of products by enzymatic action comprising a plurality of reaction tanks connected in series; a supply tank for a substrate; a conduit connecting said supply tank with the first reaction tank in the series; an ultrafilter adapted to separate an enzyme from its reaction product associated with each reaction tank, wherein each of said ultra filters being provided with an inlet, an outlet for removal of retentate and an outlet for removal of filtrate; separate conduits leading from each reaction tank to the inlet of ultrafilter and leading from the outlet of each ultrafilter back into each reaction tank, the said conduits forming a closed circuit system between each reaction tank and ultrafilter; a duct connecting the respective filtrate removal outlet with the next reaction tank; a discharge outlet for the filtrate of the last ultrafilter; means for collecting the product received from said discharge outlet; conduits connecting each reaction tank with each preceding reaction tank; pump means for recirculating partly spent enzymes through said conduits and tanks; a supply tank for fresh enzyme connected to the last reaction tank so as to cause the fresh enzyme and the partly spent enzyme to move through said reaction tanks in countercurrent to the product formed in said reaction tanks.

* * * * *